US011174322B2

(12) United States Patent
Alain et al.

(10) Patent No.: US 11,174,322 B2
(45) Date of Patent: Nov. 16, 2021

(54) ANTIBODIES AND PEPTIDES TO TREAT HCMV RELATED DISEASES

(71) Applicants: INSERM (Institut National de la Santé et de la Recherche Médicale), Paris (FR); Centre Hospitalier Régional Universitaire de Limoges, Limoges (FR); Université de Limoges, Limoges (FR)

(72) Inventors: Sophie Alain, Limoges (FR); Gaëtan Ligat, Limoges (FR); Sébastien Hantz, Limoges (FR); Anthony Couvreux, Limoges (FR)

(73) Assignees: INSERM (Institut National de la Santé et de la Recherche Médicale), Paris (FR); CENTRE HOSPITALIER Régional Universitaire de Limoges, Limoges (FR); Universitéde Limoges, Limoges (FR)

( * ) Notice: Subject to any disclaimer, the term of this patent is extended or adjusted under 35 U.S.C. 154(b) by 0 days.

(21) Appl. No.: 16/633,875

(22) PCT Filed: Jul. 19, 2018

(86) PCT No.: PCT/EP2018/069607

§ 371 (c)(1),
(2) Date: Jan. 24, 2020

(87) PCT Pub. No.: WO2019/020480

PCT Pub. Date: Jan. 31, 2019

(65) Prior Publication Data

US 2020/0207873 A1 Jul. 2, 2020

(30) Foreign Application Priority Data

Jul. 24, 2017 (EP) .................................... 17305987

(51) Int. Cl.

| | |
|---|---|
| ***C07K 16/40*** | (2006.01) |
| ***C07K 7/06*** | (2006.01) |
| ***C07K 7/08*** | (2006.01) |
| ***C07K 16/08*** | (2006.01) |
| ***C07K 4/02*** | (2006.01) |
| ***C07K 14/045*** | (2006.01) |
| ***A61K 38/00*** | (2006.01) |

(52) U.S. Cl.

CPC ................ *C07K 16/40* (2013.01); *C07K 4/02* (2013.01); *C07K 7/06* (2013.01); *C07K 7/08* (2013.01); *C07K 14/045* (2013.01); *C07K 16/085* (2013.01); *A61K 38/00* (2013.01); *C07K 2317/24* (2013.01)

(58) Field of Classification Search

CPC ........ C07K 16/40; C07K 14/045; C07K 4/02; C07K 16/085; C07K 7/06; C07K 7/08; C07K 2317/24; C07K 2317/34; C07K 16/088; A61K 38/00

See application file for complete search history.

(56) References Cited

U.S. PATENT DOCUMENTS

| | | | | |
|---|---|---|---|---|
| 2003/0165537 A1* | 9/2003 | Fehler | A61P 31/12 | 424/199.1 |
| 2003/0171277 A1 | 9/2003 | Fogelman et al. | | |
| 2005/0064394 A1* | 3/2005 | Liu | C07K 14/005 | 435/5 |
| 2016/0159864 A1* | 6/2016 | Carfi | A61K 39/12 | 424/186.1 |

FOREIGN PATENT DOCUMENTS

| | | |
|---|---|---|
| WO | 2008-095677 A1 | 8/2008 |
| WO | 2009/021254 A1 | 2/2009 |

OTHER PUBLICATIONS

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000; 165(8):4505-14. (Year: 2000).*

Kussie PH, Parhami-Seren B, Wysocki LJ, Margolies MN. A single engineered amino acid substitution changes antibody fine specificity. J Immunol. Jan. 1, 1994;152(1): 146-52. (Year: 1994).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. NatCommun. Mar. 30, 2015;6:6714. (Year: 2015).*

Sela-Culang I, Kunik V, Ofran Y. The structural basis of antibody-antigen recognition. Front Immunol. Oct. 8, 2013;4:302. (Year: 2013).*

(Continued)

*Primary Examiner* — Rachel B Gill

(74) *Attorney, Agent, or Firm* — W&C IP

(57) ABSTRACT

The present invention relates to the treatment of HCMV relates diseases. The inventors conducted a study to find an essential domain of pUL56 for its interaction with pUL89 which is important in the effect of the CMV. Sequences alignments allowed them to predict one sequence in C-terminal of pUL56 potentially necessary for interaction with pUL89. BAC mutagenesis and AlphaLISA technologies using purified proteins allowed to validate that the short sequence $_{671}$WMVVKYMGFF$_{680}$ (SEQ ID NO: 1) in C-terminal of pUL56 is involved in interaction with pUL89. Knowing this important information, antibodies directed against this sequence or peptides derived from this sequence could be useful to invalidate the interaction of pUL56 to pUL89 and thus to treat HCMV related diseases. Thus, the present invention relates to an isolated anti-pUL56 antibody, binding to the SEQ ID NO:1 or a peptide comprising the amino acids sequence: WMVVKYMGFF (SEQ ID NO: 1) or a function-conservative variant thereof for use in the treatment of HCMV related diseases.

8 Claims, 3 Drawing Sheets

Figure 1:
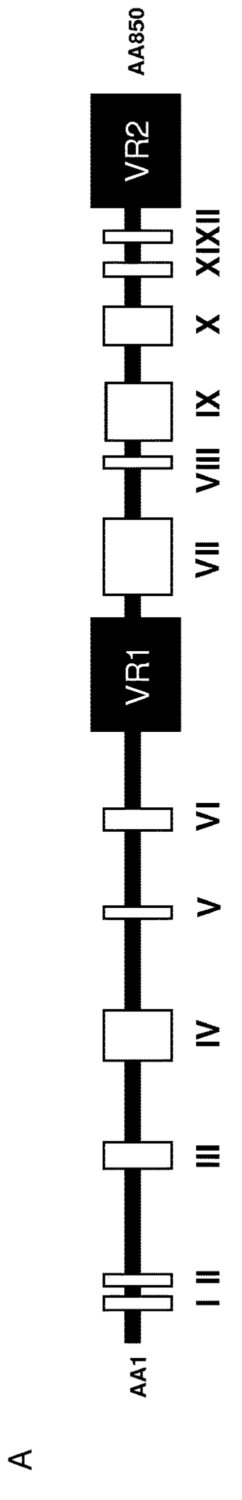

Specification includes a Sequence Listing.

(56) References Cited

OTHER PUBLICATIONS

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2016).*

Tsuchiya Y, Mizuguchi K. The diversity of H3 loops determines the antigen-binding tendencies of antibody CDR loops. Protein Sci. Apr. 2016;25(4):815-25. Epub Jan. 20, 2016. (Year: 2016).*

Collis AV, Brouwer AP, Martin AC. Analysis of the antigen combining site: correlations between length and sequence composition of the hypervariable loops and the nature of the antigen. J Mol Biol. Jan. 10, 2003;325(2):337-54. (Year: 2003).*

Trimpert J, Groenke N, Kunec D, Osterrieder N, McMahon DP. DNA packaging terminase subunit 2 [Gallid alphaherpesvirus 2], GenBank: AUB50942.1. Dep. Dec. 12, 2017.*

Pilorge L, Burrel S, Ait-Arkoub Z, Agut H, Boutolleau D. DNA packaging terminase complex subunit 2 [Human betaherpesvirus 5], GenBank: AIL27871.1. Dep. Aug. 26, 2015.*

Champier G, Couvreux A, Hantz S, Rametti A, Mazeron MC, Bouaziz S, Denis F, Alain S. Putative functional domains of human cytomegalovirus pUL56 involved in dimerization and benzimidazole D-ribonucleoside activity. AntivirTher. 2008;13(5):643-54. PMID: 18771048.*

Hwang JS, Bogner E. ATPase activity of the terminase subunit pUL56 of human cytomegalovirus. J Biol Chern. Mar. 1, 2002;277(9): 6943-8. Epub Dec. 13, 2001. (Year: 2002).*

Chee MS, Bankier AT, Beck S, Bohni R, Brown CM, Cerny R, Horsnell T, Hutchison CA 3rd, Kouzarides T, Martignetti JA, et al. Analysis of the protein-coding content of the sequence of human cytomegalovirus strain AD169. CurrTop Microbiol Immunol. 1990; 154:125-69. (Year: 1990).*

Chee MS et al. Human cytomegalovirus strain AD169 complete genome. GenBank: X17403.1. 1990. (Year: 1990).*

Thoma C, Borst E, Messerle M, Rieger M, Hwang JS, Bogner E. Identification of the interaction domain of the small terminase subunit pUL89 with the large subunit pUL56 of human cytomegalovirus. Biochemistry. Jul. 25, 2006;45(29):8855-63. (Year: 2006).*

Champier G, Couvreux A, Hantz S, Rametti A, Mazeron MC, Bouaziz S, Denis F, Alain S. Putative functional domains of human cytomegalovirus pUL56 involved in dimerization and benzimidazole D-ribonucleoside activity. Antivir Ther. 2008;13(5):643-54. (Year: 2008).*

Bogner E, Radsak K, Stinski MF. The gene product of human cytomegalovirus open reading frame UL56 binds the pac motif and has specific nuclease activity. J Virol. Mar. 1998;72(3):2259-64. (Year: 1998).*

Bradshaw et al.; "Localization of Antigenic Sites on Human Cytomegalovirus Virion Structural Proteins Encloded by UL48 and UL56"; Virology, vol. 205, Jan. 1, 1994, pp. 321-328.

Borst et al.; "The Human Cytomegalovirus UL51 Protein is Essential for Viral Genome Cleavage-Packaging and Interacts with the Terinase Subunits pUL56 and pUL89"; Journal of Virology, vol. 87, No. 3, Nov. 21, 2012, pp. 1720-1732.

Bogner et al.; "The Gene Product of Human Cytomegalovirus Open Reading Frame UL56 Binds the pac Motif and has Specific Nuclease Activity"; Journal of Virology, vol. 72, No. 3, Mar. 1, 1998, pp. 2259-2264.

Foung et al.; "Human monoclonal antibodies to human cytomegalovirus"; Journal of Infection Diseases, vol. 159, No. 3, Mar. 1, 1989, pp. 436-443.

BOGNER; "Human cytomegalovirus terminase as a target for antiviral chemotherapy"; Reviews in Medical Virology, vol. 12, No. 2, Jan. 1, 2002, pp. 115-127.

Ligat et al.; "Identification of a short sequence in the HCMV terminase pUL56 essential for interaction with pUL89 subunit"; Scientific Reports, vol. 7. No. 1, Jan. 1, 2017, the whole document.

* cited by examiner

B

| | | |
|---|---|---|
| | 670 680 | |
| **ALPHAHERPES** | | |
| HSV_1 | GSGADWAVSEFQRFYCFDGI | (SEQ ID NO:6) |
| HSV_2 | GSGADWAVSEFQKFYCFDGV | (SEQ ID NO:7) |
| CeHV_1 | -RSCDWMTSEFRRFYNFAGI | (SEQ ID NO:8) |
| CeHV_2 | -NHREWMVSEYKEFYKFPPV | (SEQ ID NO:9) |
| EHV_1 | -AKGDWSISEFQRFYCFEGV | (SEQ ID NO:10) |
| GaHV_3 | CSSSDWIVSKFRGFYDFDGI | (SEQ ID NO:11) |
| MeHV_1 | NNTSSWIISKFRGFYDFGGV | (SEQ ID NO:12) |
| HHV_3 | -VGSNWLLSPFRGFYCFSGV | (SEQ ID NO:13) |
| SUID | ---RDWCVSEFRGFYRFQT- | (SEQ ID NO:14) |
| GaHV_1 | -RSCDWMTSEFRRFYNFAGI | (SEQ ID NO:15) |
| GaHV_2 | SRKTDWTVSKFRGFYDFSTI | (SEQ ID NO:16) |
| **BETAHERPES** | | |
| AD169 | VYPSEWMVVKYMGFFNFSDC | (SEQ ID NO:17) |
| HHV_6_B | IHPRVWMVCEYNEFFNFSGV | (SEQ ID NO:18) |
| HHB_6_A_GS | IHPSVWMVCEYNEFFNFSGV | (SEQ ID NO:19) |
| CCMV | VYPSEWMVVKYMSFFNFSEC | (SEQ ID NO:20) |
| RhCMV | VVPSDWMTVGYMGFFRFADI | (SEQ ID NO:21) |
| MCMV | VVPSDWMTVGYMGFFRFADI | (SEQ ID NO:22) |
| RCMV | AEPGDWMVAGYQGFFSFVDV | (SEQ ID NO:23) |
| **GAMMAHERPES** | | |
| HHV_8 | IEPKDWIEPNFNQFYSFEN- | (SEQ ID NO:24) |
| HHV_4_1 | IEPSDWIETSFNSFYSVPG- | (SEQ ID NO:25) |
| HHV_4_2 | IEPSDWIETSFNSFYSVPG- | (SEQ ID NO:26) |
| SSP | hhhhhhhhhhhhhhhhhhhh | |

Figure 1 B

ANTIBODIES AND PEPTIDES TO TREAT HCMV RELATED DISEASES

FIELD OF THE INVENTION

The present invention relates to an isolated anti-pUL56 antibody, wherein said antibody binds to an epitope of the pUL56 protein comprising residues 671 to 680 of the amino acid sequence SEQ ID NO:2. The invention also relates to a peptide comprising the amino acids sequence: WMVVKYMGFF (SEQ ID NO: 1) or a function-conservative variant thereof.

BACKGROUND OF THE INVENTION

Human cytomegalovirus (HCMV), a beta herpesvirus, can cause serious diseases in immunocompromised patients. Current antiviral inhibitors (ganciclovir, cidofovir and foscarnet) all target the viral DNA polymerase. They have adverse effects and prolonged treatment can select for drug resistance mutations either in the viral polymerase pUL54, the kinase pUL97 or both of them (Hantz et al., 2010). Thus, we need new drugs targeting others stages of replication. The terminase complex is highly specific for HCMV, has no counterpart in the human organism, and thus represents a target of choice for new antivirals development. This has been confirmed by the recent development of letermovir in the transplant setting (Lischka et al., 2010; Melendez and Razonable, 2015).

DNA packaging process requires several proteins such as pUL56 and pUL89, the large and small terminase subunits, respectively. Recently, four additional proteins were shown to be also implicated in this process, namely, pUL51, pUL52, pUL77, pUL93 (Borst et al., 2008; Borst et al., 2013; Borst et al., 2016; Köppen-Rung et al., 2016; DeRussy and Tandon, 2015; DeRussy et al., 2016). This process is driven by specific interaction of protein-DNA and protein-protein to cleave and package unit length genomic DNA into an empty capsid.

Evidence suggests that the large subunit pUL56 has a crucial role in DNA cleavage/packaging, containing many of the functional sites required for this process like interaction with the portal protein pUL104, endonuclease activity, and more interestingly an ATP-binding site (amino acids 709 to 723) (Scholz et al., 2003). Although the association between pUL56 and pUL89 has already been reported, the residues of pUL56 involved in the terminase complex integrity are still unknown (Hwang and Bogner, 2002; Thoma et al., 2006). Nevertheless, co-immunoprecipitation experiments showing an interaction between the C-terminal half of pUL56 (pUL56-Cter) and pUL89 were confirmed by other results (Hwang and Bogner, 2002; Thoma et al., 2006).

SUMMARY OF THE INVENTION

Because knowledge of terminase functional and interaction domains is important both for the development of drugs targeting the DNA packaging stage and for the improvement of existing ones such as letermovir, the aim of the current study is to identify a minimum peptide of pUL56 with a putative key role in its interaction with pUL89. Sequence alignments encouraged us to focus on the putative involvement of one part of the pUL56 sequence into its interface with pUL89. BAC mutagenesis and Alpha technology using purified proteins subsequently validated that the aromatic rich peptide $_{671}$WMVVKYMGFF$_{680}$ (SEQ ID NO: 1) pUL56(671-680) in the C-terminal of pUL56 is involved in interaction with pUL89.

Thus, the present invention relates to an isolated anti-pUL56 antibody, wherein said antibody binds to an epitope of the pUL56 protein comprising residues 671 to 680 of the amino acid sequence of SEQ ID NO:2. The invention also relates to a peptide comprising the amino acids sequence: WMVVKYMGFF (SEQ ID NO: 1) or a function-conservative variant thereof. In particular embodiment, the invention is described by the claims.

DETAILED DESCRIPTION OF THE INVENTION

The inventors clearly showed the importance of the short sequence $_{671}$WMVVKYMGFF$_{680}$ (SEQ ID NO:1) localized in the C-terminal part of pUL56 in the interaction of pUL56 with pUL89. Knowing this important information, antibodies directed against this sequence or peptides derived from this sequence could be useful to invalidate the interaction of pUL56 to pUL89 and thus to treat HCMV related diseases.

Antibodies of the Invention

A first object of the invention relates to an isolated anti-pUL56 antibody, wherein said antibody binds to an epitope of the pUL56 protein comprising residues 671 to 680 of the amino acid sequence SEQ ID NO:2.

```
Sequence of the pUL56 of the human cytomegalovirus
(SEQ ID NO: 2):
MEMNLLQKLCVVCSKCNEYAMELECLKYCDPNVLLAESTPFKRNAAAIVY

LYRKIYPEVVAQNRTQSSLLTLYLEMLLKALHEDTALLDRALMAYSRQPD

RAAFYRTVLRLDRCDRHHTVELQFTDNVRFSVSLATLNDIERFLCKMNYV

YGILAPEAGLEVCAQLLELLRRLCGISPVARQEVYVEGTTCAQCYEELTI

IPNQGRSLNKRLQGLLCNHIAVHRPSSQSDVNIQTVEQDLLDLTTRIPHL

AGVLSALKSLFSSSSAYHSYIQEAEEALREYNLFTDIPERIYSLSDFTYW

SRTSEVIVKRVGITIQQLNVYHQLCRALMNGISRHLYGEDVEDIFVLGEK

ALDGEERMFVGSVFAAPNRIIDLITSLSIQAFEDNPVFNKLHESNEMYTK

IKHILEEIRRPLPDGTGGDGPEGEAIHLRGREAMSGTGTTLMTASNSSNS

STHSQRNNGGGGRARGGGKKAVGGGANGQDGDGSENGLRVRNCDEHEALD

LVDARSRIHNVTREVNVRKRAYLQKVSEVGYGKVIRCIKTQERLTSKLID

VNLVGPLCLDFISKLMNGFLYRSQYHQDQDVVDVGDQFTYDEHLYVVNNL

IHKSLPVESLPLLGQQIYELCNGPLFTHCTDRYPLSHNVDMAYACDNAGV

LPHVKDDLVKCAEGTVYPSEWMVVKYMGFFNFSDCQDLNVLQKEMWMHVR

ELVLSVALYNETFGKQLSIACLRDELHPDRDVILTYNKEWPLLLRHEGNL

YKSKDLYLLLYRHLSRPDESGDVPTAPVAKPSTLTAAAAVSGAFREPDRP

WLPSPYPSSSTAGVSRRVRATRKRPRRASSLLDLARDEHGIQDLVPGSLR
```

In one embodiment, the isolated antibody of the invention is specific to the peptidic sequence SEQ ID NO: 1 of the protein pUL56 which is responsible of the interaction of pUL56 with pUL89.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In one embodiment, the antibody of the invention is monoclonal antibody.

In one embodiment, the antibody of the invention is a chimeric antibody, particularly a chimeric mouse/human antibody.

According to the invention, the term "chimeric antibody" refers to an antibody which comprises a VH domain and a VL domain of a non-human antibody, and a CH domain and a CL domain of a human antibody.

In some embodiments, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

In another embodiment, the antibody of the invention is a humanized antibody. In particular, in said humanized antibody, the variable domain comprises human acceptor frameworks regions, and optionally human constant domain where present, and non-human donor CDRs, such as mouse CDRs.

In another embodiment, the antibody of the invention is a caninized or primatized based on the same methods of humanization.

According to the invention, the term "humanized antibody" refers to an antibody having variable region framework and constant regions from a human antibody but retains the CDRs of a previous non-human antibody.

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

In some embodiments the antibody of the invention is a human antibody.

As used herein the term "human antibody is intended to include antibodies having variable and constant regions derived from human immunoglobulin sequences. The human antibodies of the present invention may include amino acid residues not encoded by human immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Human antibodies can be produced using various techniques known in the art. Human antibodies are described generally in van Dijk and van de Winkel, cur. Opin. Pharmacol. 5; 368-74 (2001) and Lonberg, cur. Opin. Immunol. 20; 450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23; 1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application publication No. US 2007/0061900, describing VELOCIMOUSE® technology. Human variable regions from intact antibodies generated by such animals may be further modified, e.g., by combining with a different human constant region Human antibodies can also be made by hybridoma-based methods. Human myeloma and mouse-human heteromyeloma cell lines for the production of human monoclonal antibodies have been described. (See, e.g., Kozbor J. Immunol., 13: 3001 (1984);

Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human igM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005). Fully human antibodies can also be derived from phage-display libraries (as disclosed in Hoogenboom et al., 1991, J. Mol. Biol. 227:381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT publication No. WO 99/10494. Human antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In one embodiment, the antibody of the invention is an antigen biding fragment selected from the group consisting of a Fab, a F(ab)'2, a single domain antibody, a ScFv, a Sc(Fv)2, a diabody, a triabody, a tetrabody, an unibody, a minibody, a maxibody, a small modular immunopharmaceutical (SMIP), minimal recognition units consisting of the amino acid residues that mimic the hypervariable region of an antibody as an isolated complementary determining region (CDR).

The term "antigen binding fragment" of an antibody, as used herein, refers to one or more fragments of an intact antibody that retain the ability to specifically binds to a given antigen (e.g., pUL56). Antigen biding functions of an antibody can be performed by fragments of an intact antibody. Examples of biding fragments encompassed within the term antigen biding fragment of an antibody include a Fab fragment, a monovalent fragment consisting of the VL, VH, CL and CH1 domains; a Fab' fragment, a monovalent fragment consisting of the VL, VH, CL, CH1 domains and hinge region; a $F(ab')_2$ fragment, a bivalent fragment comprising two Fab' fragments linked by a disulfide bridge at the hinge region; an Fd fragment consisting of VH domains of a single arm of an antibody; a single domain antibody (sdAb) fragment (Ward et al., 1989 Nature 341:544-546), which consists of a VH domain or a VL domain; and an isolated complementary determining region (CDR). Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (ScFv); see, e.g., Bird et al., 1989 Science 242:423-426; and Huston et al., 1988 proc. Natl. Acad. Sci. 85:5879-5883). "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2. Such single chain antibodies include one or more antigen biding portions or fragments of an antibody. These antibody fragments are obtained using conventional techniques known to those skilled in the art, and the fragments are screened for utility in the same manner as are intact antibodies. A unibody is another type of antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies. Antigen binding fragments can be incorporated into single domain antibodies, SMIP, maxibodies, minibodies, intrabodies, diabodies, triabodies and tetrabodies (see, e.g., Hollinger and Hudson, 2005, Nature Biotechnology, 23, 9, 1126-1136). The term "diabodies" "tribodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Antigen biding fragments can be incorporated into single chain molecules comprising a pair of tandem Fv segments (VH-CH1-VH-CH1) Which, together with complementary light chain polypeptides, form a pair of antigen binding regions (Zapata et al., 1995 Protein Eng. 8(10); 1057-1062 and U.S. Pat. No. 5,641,870).

The Fab of the present invention can be obtained by treating an antibody which specifically reacts with pUL56, with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with pUL56, with a protease, pepsin. Also, the F(ab')2 can be produced by binding Fab' described below via a thioether bond or a disulfide bond.

The Fab' of the present invention can be obtained treating F(ab')2 which specifically reacts with pUL56, with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., W098/45322; WO 87/02671; U.S. Pat. Nos. 5,859,205; 5,585,089; 4,816,567; EP0173494).

Domain Antibodies (dAbs) are the smallest functional binding units of antibodies—molecular weight approximately 13 kDa—and correspond to the variable regions of either the heavy (VH) or light (VL) chains of antibodies. Further details on domain antibodies and methods of their production are found in U.S. Pat. Nos. 6,291,158; 6,582,915; 6,593,081; 6,172,197; and 6,696,245; US 2004/0110941; EP 1433846, 0368684 and 0616640; WO 2005/035572, 2004/101790, 2004/081026, 2004/058821, 2004/003019 and 2003/002609, each of which is herein incorporated by reference in its entirety.

UniBodies are another antibody fragment technology, based upon the removal of the hinge region of IgG4 antibodies. The deletion of the hinge region results in a molecule that is essentially half the size of a traditional IgG4 antibody and has a univalent binding region rather than a bivalent binding region. Furthermore, because UniBodies are about smaller, they may show better distribution over larger solid tumors with potentially advantageous efficacy. Further details on UniBodies may be obtained by reference to WO 2007/059782, which is incorporated by reference in its entirety.

The present invention also provides for an isolated anti-pUL56 single domain antibody, wherein said antibody binds to an epitope of the pUL56 protein comprising residues 671 to 680 of the amino acid sequence SEQ ID NO:2.

As used herein the term "single domain antibody" has its general meaning in the art and refers to the single heavy chain variable domain of antibodies of the type that can be found in Camelid mammals which are naturally devoid of light chains. Such single domain antibody are also called VHH or "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents to detect antigens that are otherwise cryptic using classical immunological techniques, and as possible therapeutic agents. Thus yet another consequence of small size is that a nanobody can inhibit as a result of binding to a specific site in a groove or narrow cleft of a target protein, and hence can serve in a capacity that more closely resembles the function of a classical low molecular weight drug than that of a classical antibody. The low molecular weight and compact size further result in nanobodies being extremely thermostable, stable to extreme pH and to proteolytic digestion, and poorly antigenic. Another consequence is that nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. The amino acid sequence and structure of a single domain antibody can be considered to be comprised of four framework regions or "FRs" which are referred to in the art and herein as "Framework region 1" or "FR1 "; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (imgt.cines.fr/).

Camel Ig can be modified by genetic engineering to yield a small protein having high affinity for a target, resulting in a low molecular weight antibody-derived protein known as a "nanobody" or "VHH". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. In certain embodiments herein, the camelid antibody or nanobody is naturally produced in the camelid animal, i.e., is produced by the camelid following immunization with pUL56 or a peptide fragment thereof, using techniques described herein for other antibodies. Alternatively, the pUL56-binding camelid nanobody is engineered, i.e., produced by selection for example from a library of phage displaying appropriately mutagenized camelid nanobody proteins using panning procedures with pUL56 as a target.

In some embodiments, the single domain antibody is a "humanized" single domain antibody.

As used herein the term "humanized" refers to a single domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favorable properties of single domain antibodies of the invention. The one skilled in the art is able to determine and select suitable humanizing substitutions or suitable combinations of humanizing substitutions.

A further aspect of the invention refers to a polypeptide comprising at least one single domain antibody of the invention.

Typically, the polypeptide of the invention comprises a single domain antibody of the invention, which is fused at its N-terminal end, at its C-terminal end, or both at its N-terminal end and at its C-terminal end to at least one further amino acid sequence, i.e. so as to provide a fusion protein. According to the invention the polypeptides that comprise a sole single domain antibody are referred to herein as "monovalent" polypeptides. Polypeptides that comprise or essentially consist of two or more single domain antibodies according to the invention are referred to herein as "multivalent" polypeptides.

According to the invention, the single domain antibodies and polypeptides of the invention may be produced by conventional automated peptide synthesis methods or by recombinant expression. General principles for designing and making proteins are well known to those of skill in the art. The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art. As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

In another aspect, the invention provides an antibody that competes for binding to the SEQ ID NO:1 with the antibody of the invention.

As used herein, the term "binding" in the context of the binding of an antibody to a predetermined antigen or epitope typically is a binding with an affinity corresponding to a KD of about 10-7 M or less, such as about 10-8 M or less, such as about 10-9 M or less, about 10-10 M or less, or about 10-11 M or even less when determined by for instance surface plasmon resonance (SPR) technology in a BIAcore 3000 instrument using a soluble form of the antigen as the ligand and the antibody as the analyte. BIACORE® (GE Healthcare, Piscataway, N.J.) is one of a variety of surface plasmon resonance assay formats that are routinely used to epitope bin panels of monoclonal antibodies. Typically, an antibody binds to the predetermined antigen with an affinity corresponding to a KD that is at least ten-fold lower, such as at least 100-fold lower, for instance at least 1,000-fold lower, such as at least 10,000-fold lower, for instance at least 100,000-fold lower than its KD for binding to a non-specific antigen (e.g., BSA, casein), which is not identical or closely related to the predetermined antigen. When the KD of the antibody is very low (that is, the antibody has a high affinity), then the KD with which it binds the antigen is typically at least 10,000-fold lower than its KD for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Additional antibodies can be identified based on their ability to cross-compete (e.g., to competitively inhibit the binding of, in a statistically significant manner) with other antibodies of the invention in standard [antigen] binding assays. The ability of a test antibody to inhibit the binding of antibodies of the present invention to [antigen] demonstrates that the test antibody can compete with that antibody for binding to [antigen]; such an antibody may, according to non-limiting theory, bind to the same or a related (e.g., a structurally similar or spatially proximal) epitope on [antigen] as the antibody with which it competes. Thus, another aspect of the invention provides antibodies that bind to the same antigen as, and compete with, the antibodies disclosed herein. As used herein, an antibody "competes" for binding when the competing antibody inhibits [antigen] binding of an antibody or antigen binding fragment of the invention by more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% in the presence of an equimolar concentration of competing antibody.

In other embodiments the antibodies or antigen binding fragments of the invention bind to one or more epitopes of [antigen]. In some embodiments, the epitopes to which the present antibodies or antigen binding fragments bind are linear epitopes. In other embodiments, the epitopes to which the present antibodies or antigen binding fragments bind are non-linear, conformational epitopes.

The antibodies of the invention may be assayed for specific binding by any method known in the art. Many different competitive binding assay format(s) can be used for epitope binding. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York).

In a particular embodiment, the antibodies of the invention (chimeric or monoclonal antibodies or single domain antibody) can be used for the diagnostic of HCMV related diseases.

The antibodies of the invention may be particularly useful to detect the amino acids sequence SEQ ID NO: 1 and thus the protein pUL56 of the HCMV. Thus, the antibodies may be used to detect the HCMV and thus may be useful for the diagnostic of HCMV related diseases in a sample of subject suspected to have a HCMV related disease.

In particularly, the antibodies of the invention may be used in an ELISA method. ELISA method can be used, wherein the wells of a microtiter plate are coated with a set of antibodies against the protein/peptide to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

Other immunodiagnostic techniques, including immunoassays such as competition, direct reaction, or sandwich type assays can be used according to the invention.

Nucleic Acid Sequence

Accordingly, a further object of the invention relates to a nucleic acid molecule encoding an antibody according to the invention. More particularly the nucleic acid molecule encodes an antibody which binds to an epitope of the pUL56 protein comprising residues 671 to 680 of the amino acid sequence of SEQ ID NO:2.

Vectors

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further aspect of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

Host Cells

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

Peptides of the Invention

A second object of the invention relates to an isolated peptide comprising an amino acid sequence of formula (I):

W-Xaa1-Xaa2-Xaa3-Xaa4-Xaa5-Xaa6-Xaa7-F-Xaa8,
wherein:

Xaa1, Xaa2-Xaa3-Xaa4, Xaa6 and Xaa7 is the amino acids Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) or pentafluorophenylalanine; and Xaa5 and Xaa8 is the amino acids Phenylalanine (F) or Tyrosine (Y).

A particular embodiment of the invention relates to an isolated peptide consisting of an amino acid sequence of formula (I):

W-Xaa1-Xaa2-Xaa3-Xaa4-Xaa5-Xaa6-Xaa7-F-Xaa8,
wherein:

Xaa1, Xaa2-Xaa3-Xaa4, Xaa6 and Xaa7 is the amino acids Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) or pentafluorophenylalanine; and Xaa5 and Xaa8 is the amino acids Phenylalanine (F) or Tyrosine (Y).

In a particular embodiment, the amino acids Xaa1 is Methionine (M), the amino acids Xaa2 is Valine (V), Xaa3 is Valine (V), Xaa4 is Lysine (K), Xaa5 is Phenylalanine (F), or Tyrosine (Y), Xaa6 is Methionine (M), Xaa7 is Glycine (G) and Xaa8 is Phenylalanine (F) or Tyrosine (Y).

In a particular embodiment the peptide of the invention comprise of the amino acids sequence: WMVVKFMGFF (SEQ ID NO:3, Variant 1), WMVVKFMGFY (SEQ ID NO:4, Variant 2), or WMVVKYMGFY (SEQ ID NO:5, Variant 3).

In a particular embodiment the peptide of the invention consists of the amino acids sequence: WMVVKFMGFF (SEQ ID NO:3), WMVVKFMGFY (SEQ ID NO:4), (SEQ ID NO:16) or WMVVKYMGFY (SEQ ID NO:5).

In a particular embodiment, the invention relates to a peptide comprising the amino acids sequence: WMVV-KYMGFF (SEQ ID NO: 1) or a function-conservative variant thereof.

In another particular embodiment, the invention relates to a peptide consisting to the amino acids sequence: WMVV-KYMGFF (SEQ ID NO: 1) or a function-conservative variant thereof.

In another embodiment, the peptide according to the invention may differ from 1, 2 or 3 amino acids to the SEQ ID NO: 1.

The invention also encompasses peptides that are function-conservative variants of the peptide comprising SEQ ID NO: 1 as described here above.

In one embodiment, the peptide of the invention comprises at least 60%, 65%, 70%, 75%, 80%, at least 85%, at least 90%, at least 95%, at least 97% or 100% of identity over said SEQ ID NO: 1, and is still able to disrupt the interaction of pUL56 with pUL89 of the HCMV.

In one embodiment, the peptide of the invention consists in the amino acid sequence as set forth in SEQ ID NO:1 or a variant thereof comprising at least 60%, 65%, 70%, 75%, 80%, 85%, 90%, 95%, 96%, 97%, 98%, 99%, 99.5% or 99.9% identity with SEQ ID NO:1 and is still able to able to disrupt the interaction of pUL56 with pUL89 of the HCMV.

To verify whether the newly generated peptides are still able to disrupt the interaction of pUL56 with pUL89 of the HCMV a test may be performed with each peptide. Foci reduction assay in 48-well plates can be used to measure the concentration of peptides required to reduce the number of foci by 50% as compared to controls to determine IC50. MRC-5 subconfluent cells are infected with AD169 at a multiplicity of infection (MOI) of 0.1 (minimal essential medium (MEM) containing 10% fetal bovine serum) and 45 min 3500 rpm 37° C. The medium is removed and cells are incubated with various peptides concentrations for five days (each peptide concentrations was tested in triplicate). The plaques are counted and the IC50 is calculated by graphic extrapolation.

In one embodiment of the invention, the peptide of the invention is an amino acid sequence of less than 30 amino acids long that comprises the amino acid sequence of formula (I) as defined here above.

In one embodiment of the invention, the peptide of the invention is an amino acid sequence of less than 25 amino acids long that comprises the amino acid sequence of formula (I) as defined here above.

In one embodiment of the invention, the peptide of the invention is an amino acid sequence of less than 20 amino acids long that comprises the amino acid sequence of formula (I) as defined here above.

In one embodiment of the invention, the peptide of the invention is an amino acid sequence of less than 15 amino acids long that comprises the amino acid sequence of formula (I) as defined here above.

In one embodiment of the invention, the peptide of the invention is an amino acid sequence of less than 30 amino acids long that comprises the amino acid sequence SEQ ID NO:1 as defined here above.

In one embodiment of the invention, the peptide of the invention is an amino acid sequence of less than 25 amino acids long that comprises the amino acid sequence SEQ ID NO:1 as defined here above.

In one embodiment of the invention, the peptide of the invention is an amino acid sequence of less than 20 amino acids long that comprises the amino acid sequence SEQ ID NO:1 as defined here above.

In one embodiment of the invention, the peptide of the invention is an amino acid sequence of less than 15 amino acids long that comprises the amino acid sequence SEQ ID NO:1 as defined here above.

As used herein, the term "Function-conservative variants" refer to those in which a given amino acid residue in a protein or enzyme has been changed (inserted, deleted or substituted) without altering the overall conformation and function of the peptide. Such variants include protein having amino acid alterations such as deletions, insertions and/or substitutions. A "deletion" refers to the absence of one or more amino acids in the protein. An "insertion" refers to the addition of one or more of amino acids in the protein. A "substitution" refers to the replacement of one or more amino acids by another amino acid residue in the protein. Typically, a given amino acid is replaced by an amino acid having similar properties (such as, for example, polarity, hydrogen bonding potential, acidic, basic, hydrophobic, aromatic, and the like). This given amino acid can be a natural amino acid or a non natural amino acid. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGA-LIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

Typically, the invention encompasses peptides substantially identical to the peptide of formula (I) or comprising SEQ ID NO:1 in which one or more residues have been conservatively substituted with a functionally similar residue and which displays the functional aspects of the peptides of formula (I) or comprising SEQ ID NO:1 as described here above, i.e. being still able to able to disrupt the interaction of pUL56 with pUL89 of the HCMV.

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The term "conservative substitution" also includes the use of a chemically derivatized residue in place of a non-derivatized residue. "Chemical derivative" refers to a subject peptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides that contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The term "conservative substitution" also includes the use of non natural amino acids aimed to control and stabilize peptides or proteins secondary structures. These non natural amino acids are chemically modified amino acids such as prolinoamino acids, beta-amino acids, N-methylamino acids, cyclopropylamino acids, alpha, alpha-substituted amino acids as describe here below. These non natural amino acids may include also fluorinated, chlorinated, brominated- or iodinated modified amino acids.

In one embodiment, peptides of the invention may comprise a tag. A tag is an epitope-containing sequence which can be useful for the purification of the peptides. It is attached to by a variety of techniques such as affinity chromatography, for the localization of said peptide or polypeptide within a cell or a tissue sample using immunolabeling techniques, the detection of said peptide or polypeptide by immunoblotting etc. Examples of tags commonly employed in the art are the GST (glutathion-S-transferase)-tag, the FLAG™-tag, the Strep-tag™, V5 tag, myc tag, His tag etc.

In one embodiment, peptides of the invention may be labelled by a fluorescent dye. Dye-labelled fluorescent peptides are important tools in cellular studies. Peptides can be labelled on the N-terminal side or on the C-terminal side.

N-Terminal Peptide Labeling Using Amine-Reactive Fluorescent Dyes

Amine-reactive fluorescent probes are widely used to modify peptides at the N-terminal or lysine residue. A number of fluorescent amino-reactive dyes have been developed to label various peptides, and the resultant conjugates are widely used in biological applications. Three major classes of amine-reactive fluorescent reagents are currently used to label peptides: succinimidyl esters (SE), isothiocyanates and sulfonyl chlorides.

C-Terminal Labeling Using Amine-Containing Fluorescent Dyes

Amine-containing dyes are used to modify peptides using water-soluble carbodiimides (such as EDC) to convert the carboxy groups of the peptides into amide groups. Either NHS or NHSS may be used to improve the coupling efficiency of EDC-mediated protein-carboxylic acid conjugations.

In specific embodiments, it is contemplated that peptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the peptides-derived described herein for therapeutic delivery.

According to the invention, peptides may be produced by conventional automated peptide synthesis methods or by recombinant expression. General principles for designing and making proteins are well known to those of skill in the art.

Peptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. Peptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. U.S. Pat. Nos. 6,569,645; 6,043,344; 6,074,849; and 6,579,520 provide specific examples for the recombinant production of peptides and these patents are expressly incorporated herein by reference for those teachings. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the peptides-derived of the invention, it would be necessary to employ vectors comprising polynucleotide molecules for encoding the peptides-derived. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in Okayama and Berg, 1983; Cosman et al., 1986; Cosman et al., 1984; EP-A-0367566; and WO 91/18982. Other considerations for producing expression vectors are detailed in e.g., Makrides et al., 1999; Kost et al., 1999. Wurm et al., 1999 is incorporated herein as teaching factors for consideration in the large-scale transient expression in mammalian cells for recombinant protein production.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the peptide of interest (i.e., 4N1K, a variant and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

In one embodiment, the peptide of the invention is linked with at least one cell penetrating peptide.

The terms "cell penetrating peptide" or "CPP" are used interchangeably and refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refers to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. Such penetrating peptides may be those described in Fonseca S. B. et al., Advanced Drug Delivery Reviews, 2009, 61: 953-964, Johansson et al., Methods in Molecular Biology, 2011, Vol. 683, Chapter 17, in WO2004/011595 and in WO2003/011898.

In one embodiment the CPP is selected in the group consisting in but not limited to Tat peptide, polyarginines peptide, HA2-R9 peptide, Penetratin peptide, Transportan peptide, Vectocell® peptide, maurocalcine peptide, decalysine peptide, HIV-Tat derived PTD4 peptide, Hepatitis B virus Translocation Motif (PTM) peptide, mPrP1-28 peptide, POD, pVEC, EB1, Rath, CADY, Histatin 5, Antp peptide, Cyt86-101 peptide.

Acids Nucleic, Vectors, Recombinant Host Cells and Uses Thereof

Another object of the invention relates to a nucleic acid encoding an amino acids sequence comprising SEQ ID NO: 1 or a function-conservative variant thereof as described here above.

In one embodiment, said nucleic acid encoding an amino acids sequence consisting on SEQ ID NO: 1.

Nucleic acids of the invention may be produced by any technique known per se in the art, such as, without limitation, any chemical, biological, genetic or enzymatic technique, either alone or in combination(s).

Another object of the invention is an expression vector comprising a nucleic acid sequence encoding an amino sequence comprising SEQ ID NO: 1 or a function-conservative variant thereof as described here above According to the invention, expression vectors suitable for use in the invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus, lentivirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art that the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods or commercially available.

Another object of the invention is a host cell comprising an expression vector as described here above According to the invention, examples of host cells that may be used are eukaryote cells, such as animal, plant, insect and yeast cells and prokaryotes cells, such as *E. coli*. The means by which the vector carrying the gene may be introduced into the cells include, but are not limited to, microinjection, electroporation, transduction, or transfection using DEAE-dextran, lipofection, calcium phosphate or other procedures known to one skilled in the art.

In another embodiment, eukaryotic expression vectors that function in eukaryotic cells are used. Examples of such vectors include, but are not limited to, viral vectors such as retrovirus, adenovirus, adeno-associated virus, herpes virus, vaccinia virus, poxvirus, poliovirus; lentivirus, bacterial expression vectors, plasmids, such as pcDNA3 or the baculovirus transfer vectors. Preferred eukaryotic cell lines include, but are not limited to, COS cells, CHO cells, HeLa cells, NIH/3T3 cells, 293 cells (ATCC #CRL1573), T2 cells, dendritic cells, or monocytes.

Applications According to the Invention

The present invention relates to an antibody or a peptide according to the invention for use in the treatment of HCMV related diseases in a subject in need thereof. In particular, diseases which could be treat included but are not limited to glandular fever, pneumonia, retinitis, painful swallowing, diarrhea and weakness or numbness in the legs.

In another embodiment, the antibody or the peptides according to the invention may be useful to treat a baby infected during the pregnancy of his mother or to prevent the transmission of the virus to the baby during the pregnancy.

In another embodiment, the antibody or the peptides according to the invention may be useful to reduce the risk of the transmission of a HCMV infection from an HCMV-infected donor to a recipient in need thereof.

In another particular embodiment, the invention relates to an antibody or a peptide according to the invention for use in the treatment of HCMV infection in a subject in need thereof.

Thus the invention relates to an isolated anti-pUL56 antibody, wherein said antibody binds to an epitope of the pUL56 protein comprising residues 671 to 680 of the amino acid sequence SEQ ID NO:2 for use in the treatment of HCMV related diseases in a subject in need thereof.

Thus, the invention relates to a peptide of formula (I) or a peptide comprising the amino acids sequence: WMVVKYMGFF (SEQ ID NO:1) or a function-conservative variant thereof for use in the treatment of HCMV related diseases in a subject in need thereof.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

The invention also relates to a method for treating a HCMV related diseases in a subject in need thereof comprising administering to a subject in need thereof a therapeutically effective amount of an antibody or a peptide according to the invention.

Therapeutic Composition

Another object of the invention relates to a therapeutic composition comprising an antibody or a peptide according to the invention for use in the treatment of HCMV related diseases in a subject in need thereof.

In a particular embodiment, the invention relates to a therapeutic composition comprising an antibody or a peptide according to the invention for use in the treatment of HCMV infection in a subject in need thereof.

In a particular embodiment the therapeutic composition is a vaccine composition used for prophylactic used.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Pharmaceutical compositions of the present invention may comprise a further therapeutic active agent. The present invention also relates to a kit comprising an agonist, antagonist or inhibitor of the expression according to the invention and a further therapeutic active agent.

For example, anti-HCMV agents may be added to the pharmaceutical composition as described below.

Anti-HCMV agents may be the polymerase inhibitors Ganciclovir, Valganciclovir, Foscarnet or Cidofovir, or other molecules with anti-HCMV potentiel such as artesunate and its derivatives, leflunomide, everolimus, or new anti-HCMV agents such as letermovir or other anti-terminases, and maribavir or other UL97 kinase inhibitors. Or any other anti-HCMV compound further developed.

The invention will be further illustrated by the following figures and examples. However, these examples and figures should not be interpreted in any way as limiting the scope of the present invention.

FIGURES

FIG. 1: A. Structure of HCMV terminase subunit pUL56 according to Champier et al., 2008 with a putative leucine zipper pattern annotated as pUL56-LZ. B. Sequences alignment of conserved regions from 21 herpesviruses. Sequence numbering is consistent with that of AD169 residues. Key residues are highlighted as white letters on a black background. SSP: Secondary structure prediction of pUL56-LZ (h=α helix).

Figure 2:
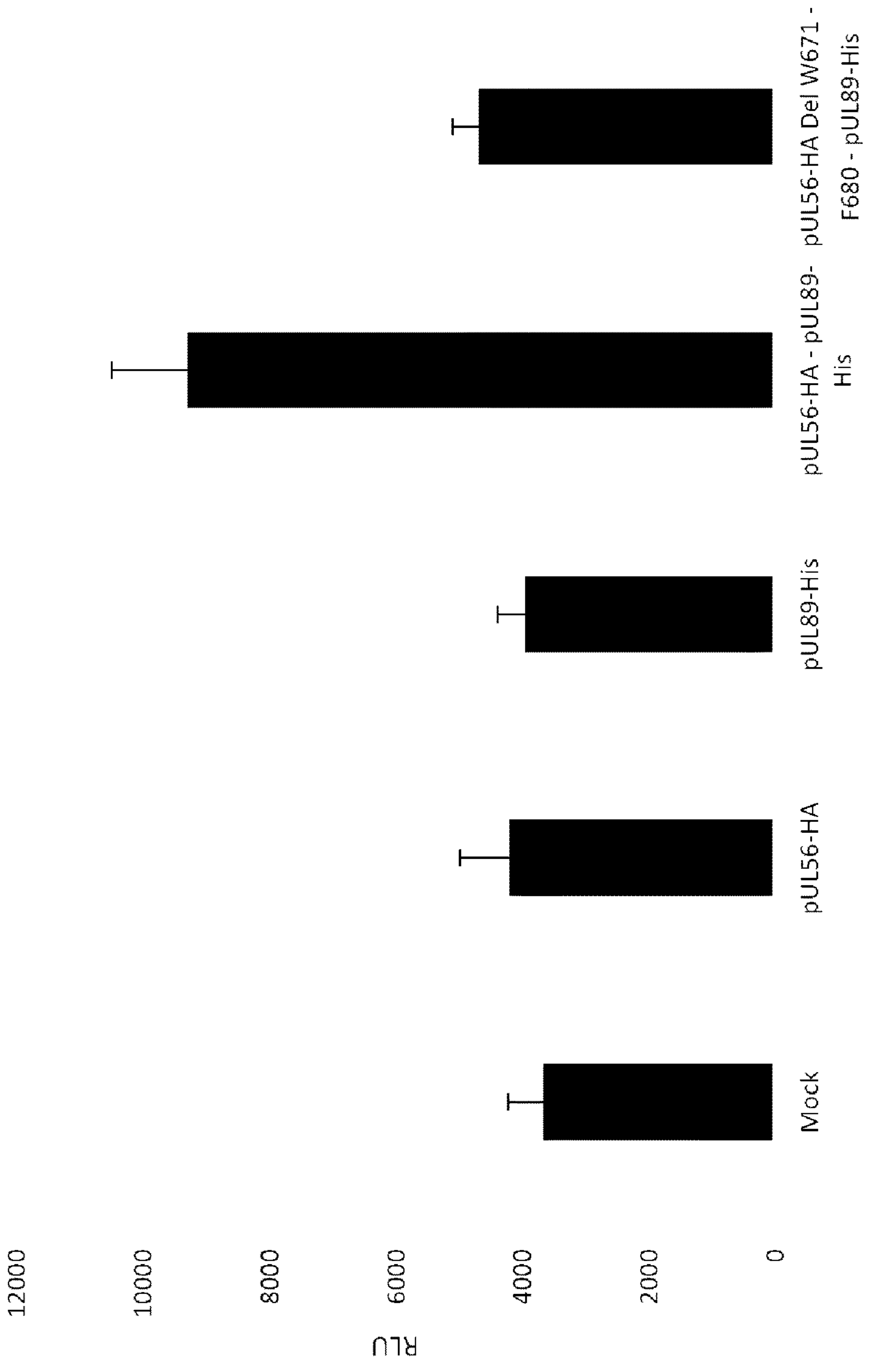

FIG. 2: Determination of pUL56 binding domains for the interaction with pUL89 Alpha assay results. The Alpha assay for the binding of full-length pUL89 (His-pUL89, 1.5E+03 nM) was performed with 5E+02 nM wild-type pUL56 (HA-pUL56) or a deletion mutant of pUL56 (HA-pUL56 Del W671-F680). As a negative control, proteins were used alone and a reaction was performed without proteins (mock). Two measures for each reaction were performed in duplicate.

EXAMPLE

Material & Methods

Identification of Conserved Patterns and Secondary Structure Prediction

The pUL56 amino acid sequence of reference strain AD169 (Chee et al., 1990) was aligned with the sequences of 21 homologous proteins from other herpesviruses, as described in supplementary table 1. Alignments were performed with Clustal Omega (Ω) multiple sequence alignment (MSA) tool provided by the EMBL-EBI bioinformatics web and programmatic tools framework (Sievers et al., 2011) (McWilliam et al., 2013) (Li et al., 2015). Secondary structure prediction was carried by Phyre2 web portal (Kelley et al., 2015).

Cells and Bacterial Strains

Human fibroblasts MRC-5 (Biomerieux, France) were cultivated at 37° C. in 5% $CO_2$ and grown in minimal essential medium (MEM) containing 10% fetal bovine serum with antibiotics. HEK293 (ATCC® CRL-1573™) were cultivated at 37° C. in 5% $CO_2$ and grown in minimal essential medium (MEM) containing 10% fetal bovine serum with antibiotics. *E. coli* strain DH5α and Stellar™ (Clontech, USA) were used for cloning procedures. *E. coli* strain GS1783 was used for BAC mutagenesis (Borst et al., 1999).

BAC Mutagenesis and Reconstitution of Mutant Viruses

Conserved domains were deleted by “en passant” mutagenesis, a two-step markerless Red recombination system for BAC mutagenesis in *E. coli* strain GS1783. UL56 point mutations were introduced into an EGFP-expressing HCMV-BAC (Borst et al., 1999) to generate several mutants (primers used for mutagenesis are described in Table I). Presence of mutations in UL56 gene of each virus was confirmed by sequencing prior to transfection. The HCMV-BAC contains an enhanced green fluorescent protein (EGFP) gene in the unique short region and was derived from parental strain pHB5, a BAC-cloned genome of the CMV laboratory strain AD169 (Borst et al., 1999). The impact of different mutations on viral growth was assessed using transfection of mutated HCMV-BAC into human fibroblasts MRC-5 using liposomal reagent Transfast™ (Promega, USA) following manufacturer’s instructions (Hantz et al., 2013).

Library Construction and Whole-Genome DNA Sequencing

After HCMV-BAC preparation, amplicons were purified using magnetic beads (Agencourt AMPure XP) and fragmented using the Ion Xpress Plus DNA Fragment Library Preparation kit (Life Technologies). Barcodes adapters were ligated to fragment ends and 250 bp fragments were collected. The library was PCR amplified, then sequenced on the Ion Proton with the Ion Sequencing kit (Life Technologies). Bases callings were performed with Torrent Suite Software version 5.0.2. Mutations were obtained using Torrent Variant Caller using Somatic variant frequency and AD169_ATCC as reference. Mutations were then filtered against reference (Wild-type HCMV-BAC) using vcftools version 0.1.13.

Viral Immediate Early and Late Protein Expression

A transfection of mutated HCMV-BAC into human fibroblasts MRC-5 using liposomal reagent Transfast™ (Promega, USA) was performed. Cells were fixed at 5 days post transfection, and immunostaining was performed for viral immediate early (anti-IE1 antibody; Argene, France) and late (anti-gB antibody; Abcam, United Kingdom) proteins in transfected cells.

Plasmids Construction for Alpha Analysis

For protein production, the SC784 expression plasmid encoding full-length amino-terminal 3xHA-tagged pUL56 and driven by an upstream HCMV major immediate early promoter was cloned in vector pGEM3z. In-Fusion® (Clontech, USA) kit was used following manufacturer’s instructions to clone several UL56 mutants from source HCMV-BAC in SC784 plasmid. ORF encoding pUL89 is composed of two exons separated by an intron. Both exons were generated by assembling PCR from AD169 genotype and cloned into pCI-neo (Promega, USA) with His tag to obtain pCI-neo His-pUL89. Transformations were performed in DH5∝ cells. The nucleotide sequence of all constructs generated was verified by Sanger sequencing prior to use.

Transfection and Proteins Purification

HEK293 were transfected with the appropriate expression vectors by use liposomal reagent Transfast™ following manufacturer's instructions, washed and lysed 48 h later with CelLytic M (Sigma-Aldrich, USA). Lysates were cleared by centrifugation.

For purification of HA-tagged pUL56, the cell-free reaction was performed with Anti-HA Immunoprecipitation Kit according to the manufacturer's protocol (Sigma-Aldrich, USA).

For purification of His-tagged pUL89, the cell-free reaction was performed with Ni resin (Clontech, USA).

All proteins were concentrated approximately 5-fold using Pall centrifugal filters (Pall, USA), and protein concentration was determined by the Bradford method using bovine serum albumin (Sigma-Aldrich, USA) as standard protein Western Blotting SDS-PAGE was performed under reducing conditions on Mini-PROTEAN TGX Stain-Free gels (BioRad, USA). Proteins were then transferred onto a Trans-Blot Turbo PVDF Western blotting membrane (BioRad, USA). Antibody dilutions were 1:1,000 for the mouse anti-HA antibody (catalogue number: 2367, Cell Signaling, USA), mouse anti-His antibody (catalogue number: 2366, Cell Signaling, USA) and secondary anti-mouse horseradish peroxidase (HRP)-linked antibody (catalogue number: 7076, Cell Signaling, USA). Signals were visualized using the Substrat HRP Immobilon Western (Merck Millipore, USA) and a ChemiDoc imager (BioRad, USA).

Protein/Protein Interaction Analysis by Alpha

Alpha (Amplified Luminescent Proximity Homogeneous Assay) experiments were conducted according to the manufacturer's protocol (PerkinElmer, USA). Five μL of transfected MRC-5 lysate with HCMV-BAC is first disposed in wells of a 96-well AlphaPlate. The final concentration of each proteins was optimized to obtain the best value of interaction. Ten μL of each purified protein were combined (to give a final assay concentration of 500 nM of 3xHA-pUL56 and 1.5 μM of 6xHis-pUL89). Ten μL and 15 μL of 10 mg/mL of donor beads and acceptor beads, respectively, were added and incubated for 1 hour. Plates were read on a PerkinElmer EnVision™ plate reader using an excitation wavelength of 680 nm and emission detection was set at 615 nm.

Results

A Putative Conserved Protein Interface in pUL56 Subunit

Selection of a potent pUL56 fragment for pUL89 interaction was supported by three hints. First, based on the sequences alignment of pUL56 with 20 herpesviruses homologues (FIG. 2), the peptide $_{671}$WMVVKYMGFF$_{680}$ (pUL56(671-680) seems to be broadly conserved in beta-herpesviruses proteins, which supported a major role either in function or structure of pUL56. Secondly, its secondary structure is predicted as an alpha helix. Previous studies demonstrated that the peptide pUL89(580-600) implicated in the pUL56-pUL89 interface (Thoma et al., 2006) adopts an alpha helix secondary structure (Couvreux et al., 2010; Nadal et al., 2010). Moreover, wide protein-protein interfaces analyses revealed a preferential interaction of an helix of one protein with one of its counterpart (Eilers et al., 2002; Ansari and Helms, 2005). Thirdly, pUL56(671-680) is within the C-terminal part previously described to be sufficient for interaction with pUL89 (Hwang and Bogner, 2002). Interestingly, this motif belongs to the pUL56 region carrying the ATP binding site. As a parallel, pUL89(580-600) is enclosed into the endonuclease domain of pUL89 (Nadal et al., 2010). Both activities, ATPase of pUL56 on the one hand and nuclease of pUL89 on the other hand are dependent on the association between the two terminase subunits (Hwang and Bogner, 2002; Scheffczik et al., 2002). Taken together, these observations make pUL56(671-680) a good candidate to interact with pUL89.

A Deletion or Targeted Mutations of $_{671}$WMVVKYMGFF$_{680}$ (SEQ ID NO:1) pUL56 Domain Affects Viral Replication in MRC-5 Cells To evaluate the importance of the pUL56 predicted domain for viral replication, we produced by "en passant" mutagenesis recombinant EGFP-virus with complete deletion of UL56(671-680) or point mutations in this sequence. Analyse of HCMV genome confirmed that UL56 have no gene on the other strand (Bradley et al., 2009). Thus, mutations in the virus are silent on the other strand and thus cannot impact the function of another gene expressed from the other strand. To ensure that no other mutations that could have a negative impact on viral replication was introduced in the BAC backbone during the manipulations, we performed NGS sequencing on both the mutant and the original BAC. The deletion was found in 100% of the mutant BAC sequences whereas other SNPs were located in genes non essential for viral replication and represent less than 30% of the sequences both in the original BAC and in the mutant.

Unlike the wild-type HCMV-BAC, eleven days after the transfection of human fibroblasts (MRC-5 cells), we observed no foci of cytopathic effect for the mutant which has a deletion of $_{671}$WMVVKYMGFF$_{680}$ sequence (data not shown). This deletion dramatically impaired viral replication and propagation in cell-culture. In the same way, recombinant EGFP-viruses with a single or a combination of mutations among W671A, Y676A, F679A and F680A do not produce progeny virion as well. These residues were selected for mutagenesis because they are perfectly or for the less highly conserved (i.e. replaced by another aromatic amino acid) among all the 20 herpesviruses homologues of pUL56 (data not shown). To check if these deletion or mutations may disrupt another step of the viral replication, immunostaining assays were performed to detect proteins produced at immediate early and late stages of viral cycle (IE and late proteins). Expression of immediate early (IEA) and late (gB) viral genes were detected indicating that mutations have no impact on viral gene expression (data not shown). Therefore W671, Y676, F679 and F680 within pUL56(671-580) are critical amino acids for viral replication.

pUL56(671-680) is Necessary for pUL89 Association

HEK293 were transfected with SC784 and pCI-neo His-89 expression plasmids and protein-protein interactions were carried out by the Alpha assay. This technology represents a powerful method to highlight protein-protein interactions (Ullman et al., 1994) (Waller et al., 2010). Since we have no virion production for mutant viruses, we chose to study in vitro biochemical interactions after protein overexpression in HEK cells which allow introduction of tags (HA and His) for the Alpha assay.

Alpha assay needs both acceptor and donor beads. For this study, HA-coated Donor beads and 6xHis-coated Acceptor were used. A singlet of oxygen diffuses from Donor bead to the Acceptor bead, resulting in light production at 615 nm. In the absence of a specific biological interaction between proteins, singlet molecules produced by the Donor bead cannot be detected beyond 200 nm from the Acceptor bead (data not shown). First step consisted in verifying the interaction between pUL56-WT and pUL89-WT as a valuable positive control. Alpha assays with 3xHA-pUL56 and 6xHis-pUL89 results in the production of over 9,000 relative light units (RLU), over two-fold more than negative controls (3xHA-pUL56 or His-pUL89) (FIG. 2). pUL56 depleted of its W671-F680 fragment was in turn soaked with pUL89-WT and their affinity assessed by Alpha analysis. The lack of pUL56(671-680) decreased the interaction signal by 50% which is significant in this assay. These data strongly suggest that $_{671}$WMVVKYMGFF$_{680}$ is necessary for interaction with pUL89.

REFERENCES

Throughout this application, various references describe the state of the art to which this invention pertains. The disclosures of these references are hereby incorporated by reference into the present disclosure.

Ansari, S., and Helms, V. (2005). Statistical analysis of predominantly transient protein-protein interfaces. Proteins 61, 344-355.

Borst, E. M., Hahn, G., Koszinowski, U. H., and Messerle, M. (1999). Cloning of the human cytomegalovirus (HCMV) genome as an infectious bacterial artificial chromosome in *Escherichia coli*: a new approach for construction of HCMV mutants. J. Virol. 73, 8320-8329.

Borst, E. M., Wagner, K., Binz, A., Sodeik, B., and Messerle, M. (2008). The essential human cytomegalovirus gene UL52 is required for cleavage-packaging of the viral genome. J. Virol. 82, 2065-2078.

Borst, E. M., Kleine-Albers, J., Gabaev, I., Babic, M., Wagner, K., Binz, A., Degenhardt, I., Kalesse, M., Jonjic, S., Bauerfeind, R., et al. (2013). The human cytomegalovirus UL51 protein is essential for viral genome cleavage-packaging and interacts with the terminase subunits pUL56 and pUL89. J. Virol. 87, 1720-1732.

Borst, E. M., Bauerfeind, R., Binz, A., Stephan, T. M., Neuber, S., Wagner, K., Steinbrück, L., Sodeik, B., Lenac Roviš, T., Jonjić, S., et al. (2016). The Essential Human Cytomegalovirus Proteins pUL77 and pUL93 are Structural Components Necessary for Viral Genome Encapsidation. J. Virol.

Bradley, A. J., Lurain, N. S., Ghazal, P., Trivedi, U., Cunningham, C., Baluchova, K., Gatherer, D., Wilkinson, G. W. G., Dargan, D. J., and Davison, A. J. (2009). High-throughput sequence analysis of variants of human cytomegalovirus strains Towne and AD169. J. Gen. Virol. 90, 2375-2380.

Buerger, I., Reefschlaeger, J., Bender, W., Eckenberg, P., Popp, A., Weber, O., Graeper, S., Klenk, H. D., Ruebsamen-Waigmann, H., and Hallenberger, S. (2001). A novel non-nucleoside inhibitor specifically targets cytomegalovirus DNA maturation via the UL89 and UL56 gene products. J. Virol. 75, 9077-9086.

Champier, G., Couvreux, A., Hantz, S., Rametti, A., Mazeron, M.-C., Bouaziz, S., Denis, F., and Alain, S. (2008). Putative functional domains of human cytomegalovirus pUL56 involved in dimerization and benzimidazole D-ribonucleoside activity. Antivir. Ther. 13, 643-654.

Chee, M. S., Bankier, A. T., Beck, S., Bohni, R., Brown, C. M., Cerny, R., Horsnell, T., Hutchison, C. A., Kouzarides, T., and Martignetti, J. A. (1990). Analysis of the protein-coding content of the sequence of human cytomegalovirus strain AD169. Curr. Top. Microbiol. Immunol. 154, 125-169.

Chou, S. (2015). Rapid In Vitro Evolution of Human Cytomegalovirus UL56 Mutations That Confer Letermovir Resistance. Antimicrob. Agents Chemother. 59, 6588-6593.

Couvreux, A., Hantz, S., Marquant, R., Champier, G., Alain, S., Morellet, N., and Bouaziz, S. (2010). Insight into the structure of the pUL89 C-terminal domain of the human cytomegalovirus terminase complex. Proteins 78, 1520-1530.

DeRussy, B. M., and Tandon, R. (2015). Human cytomegalovirus pUL93 is required for viral genome cleavage and packaging. J. Virol.

DeRussy, B. M., Boland, M. T., and Tandon, R. (2016). Human Cytomegalovirus pUL93 Links Nucleocapsid Maturation and Nuclear Egress. J. Virol.

Eilers, M., Patel, A. B., Liu, W., and Smith, S. O. (2002). Comparison of helix interactions in membrane and soluble alpha-bundle proteins. Biophys. J. 82, 2720-2736.

Giesen, K., Radsak, K., and Bogner, E. (2000). The potential terminase subunit of human cytomegalovirus, pUL56, is translocated into the nucleus by its own nuclear localization signal and interacts with importin alpha. J. Gen. Virol. 81, 2231-2244.

Goldner, T., Hewlett, G., Ettischer, N., Ruebsamen-Schaeff, H., Zimmermann, H., and Lischka, P. (2011). The novel anticytomegalovirus compound AIC246 (Letermovir) inhibits human cytomegalovirus replication through a specific antiviral mechanism that involves the viral terminase. J. Virol. 85, 10884-10893.

Hantz, S., Garnier-Geoffroy, F., Mazeron, M.-C., Garrigue, I., Merville, P., Mengelle, C., Rostaing, L., Saint Marcoux, F., Essig, M., Rerolle, J.-P., et al. (2010). Drug-resistant cytomegalovirus in transplant recipients: a French cohort study. J. Antimicrob. Chemother. 65, 2628-2640.

Hantz, S., Cotin, S., Borst, E., Couvreux, A., Salmier, A., Garrigue, I., Merville, P., Mengelle, C., Attal, M., Messerle, M., et al. (2013). Novel DNA polymerase mutations conferring cytomegalovirus resistance: input of BAC-recombinant phenotyping and 3D model. Antiviral Res. 98, 130-134.

Hwang, J.-S., and Bogner, E. (2002). ATPase activity of the terminase subunit pUL56 of human cytomegalovirus. J. Biol. Chem. 277, 6943-6948.

Kelley, L. A., Mezulis, S., Yates, C. M., Wass, M. N., and Sternberg, M. J. E. (2015). The Phyre2 web portal for protein modeling, prediction and analysis. Nat. Protoc. 10, 845-858.

Köppen-Rung, P., Dittmer, A., and Bogner, E. (2016). Intracellular distributions of capsid-associated pUL77 of HCMV and interactions with packaging proteins and pUL93. J. Virol.

Li, W., Cowley, A., Uludag, M., Gur, T., McWilliam, H., Squizzato, S., Park, Y. M., Buso, N., and Lopez, R. (2015). The EMBL-EBI bioinformatics web and programmatic tools framework. Nucleic Acids Res. 43, W580-W584.

Lischka, P., Hewlett, G., Wunberg, T., Baumeister, J., Paulsen, D., Goldner, T., Ruebsamen-Schaeff, H., and Zimmermann, H. (2010). In vitro and in vivo activities of the novel anticytomegalovirus compound AIC246. Antimicrob. Agents Chemother. 54, 1290-1297.

McWilliam, H., Li, W., Uludag, M., Squizzato, S., Park, Y. M., Buso, N., Cowley, A. P., and Lopez, R. (2013). Analysis Tool Web Services from the EMBL-EBI. Nucleic Acids Res. 41, W597-W600.

Melendez, D. P., and Razonable, R. R. (2015). Letermovir and inhibitors of the terminase complex: a promising new class of investigational antiviral drugs against human cytomegalovirus. Infect. Drug Resist. 8, 269-277.

Nadal, M., Mas, P. J., Blanco, A. G., Arnan, C., Solà, M., Hart, D. J., and Coll, M. (2010). Structure and inhibition of herpesvirus DNA packaging terminase nuclease domain. Proc. Natl. Acad. Sci. U.S.A. 107, 16078-16083.

Scheffczik, H., Savva, C. G. W., Holzenburg, A., Kolesnikova, L., and Bogner, E. (2002). The terminase subunits pUL56 and pUL89 of human cytomegalovirus are DNA-metabolizing proteins with toroidal structure. Nucleic Acids Res. 30, 1695-1703.

Scholz, B., Rechter, S., Drach, J. C., Townsend, L. B., and Bogner, E. (2003). Identification of the ATP-binding site in the terminase subunit pUL56 of human cytomegalovirus. Nucleic Acids Res. 31, 1426-1433.

Sievers, F., Wilm, A., Dineen, D., Gibson, T. J., Karplus, K., Li, W., Lopez, R., McWilliam, H., Remmert, M., Söding, J., et al. (2011). Fast, scalable generation of high-quality protein multiple sequence alignments using Clustal Omega. Mol. Syst. Biol. 7, 539.

Thoma, C., Borst, E., Messerle, M., Rieger, M., Hwang, J.-S., and Bogner, E. (2006). Identification of the interaction domain of the small terminase subunit pUL89 with the large subunit pUL56 of human cytomegalovirus. Biochemistry (Mosc.) 45, 8855-8863.

Ullman, E. F., Kirakossian, H., Singh, S., Wu, Z. P., Irvin, B. R., Pease, J. S., Switchenko, A. C., Irvine, J. D., Dafforn, A., and Skold, C. N. (1994). Luminescent oxygen channeling immunoassay: measurement of particle binding kinetics by chemiluminescence. Proc. Natl. Acad. Sci. U.S.A. 91, 5426-5430.

Walker, M. P., Yao, N., and Hong, Z. (2003). Promising candidates for the treatment of chronic hepatitis C. Expert Opin. Investig. Drugs 12, 1269-1280.

Waller, H., Chatterji, U., Gallay, P., Parkinson, T., and Targett-Adams, P. (2010). The use of AlphaLISA technology to detect interaction between hepatitis C virus-encoded NS5A and cyclophilin A. J. Virol. Methods 165, 202-210.

The invention claimed is:

1. An isolated peptide of less than 30 amino acids comprising the amino acid sequence of formula (I):

W-Xaa1-Xaa2-Xaa3-Xaa4-Xaa5-Xaa6-Xaa7-F-Xaa8, wherein:

Xaa1, Xaa2, Xaa3, Xaa4, Xaa6 and Xaa7 are selected from the group consisting of: Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine, wherein Xaa5 and Xaa8 are Phenylalanine (F) or Tyrosine (Y), and wherein said peptide comprises a tag or a fluorescent label.

2. The isolated peptide according to claim 1, wherein the isolated peptide comprises the amino acid sequence:

WMVVKFMGFF, (SEQ ID NO: 3)

WMVVKFMGFY, (SEQ ID NO: 4)

SRKTDWTVSKFRGFYDFSTI (SEQ ID NO: 16)
or

WMVVKYMGFY. (SEQ ID NO: 5)

3. The isolated peptide according to claim 1, wherein the isolated peptide comprises the sequence of SEQ ID NO:1 or a variant thereof, wherein the variant differs from SEQ ID NO: 1 by 1, 2 or 3 amino acids.

4. A therapeutic composition comprising an isolated peptide of less than 30 amino acids comprising the amino acid sequence of formula (I): W-Xaa1-Xaa2-Xaa3-Xaa4-Xaa5-Xaa6-Xaa7-F-Xaa8, wherein: Xaa1, Xaa2, Xaa3, Xaa4, Xaa6 and Xaa7 are selected from the group consisting of: Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine; and Xaa5 and Xaa8 are Phenylalanine (F) or Tyrosine (Y).

5. A method for treating a HCMV related diseases in a subject in need thereof comprising administering to the subject a therapeutically effective amount of an isolated peptide comprising the amino acid sequence of formula (I): W-Xaa1-Xaa2-Xaa3-Xaa4-Xaa5-Xaa6-Xaa7-F-Xaa8, wherein: Xaa1, Xaa2, Xaa3, Xaa4, Xaa6 and Xaa7 are selected from the group consisting of: Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine; and Xaa5 and Xaa8 are Phenylalanine (F) or Tyrosine (Y), wherein the isolated peptide is capable of disrupting an interaction between pUL56 and pUL89.

6. An isolated peptide of less than 30 amino acids comprising the amino acid sequence of formula (I): W-Xaa1-Xaa2-Xaa3-Xaa4-Xaa5-Xaa6-Xaa7-F-Xaa8, wherein: Xaa1, Xaa2, Xaa3, Xaa4, Xaa6 and Xaa7 are selected from the group consisting of: Alanine (A), Arginine (R), Asparagine (N), Aspartic acid (D), Cysteine (C), Glutamic acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V), allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine, wherein Xaa5 and Xaa8 are Phenylalanine (F) or Tyrosine (Y), and wherein said peptide comprises a non-homologous amino acid as compared to SEQ ID NO: 2.

7. The method of claim 5, wherein the isolated polypeptide comprises the amino acid sequence WMVVKYMGFF (SEQ ID NO: 1) or a function-conservative variant thereof, wherein the variant differs from SEQ ID NO: 1 by 1, 2 or 3 conservative amino acid substitutions.

8. The method of claim 7, wherein the variant comprises the amino acid sequence: WMVVKFMGFF (SEQ ID NO:3), WMVVKFMGFY (SEQ ID NO:4), or WMVVKYMGFY (SEQ ID NO:5).

* * * * *

SEQUENCE LISTING

```
<160> NUMBER OF SEQ ID NOS: 26

<210> SEQ ID NO 1
<211> LENGTH: 10
<212> TYPE: PRT
<213> ORGANISM: Artificial
<220> FEATURE:
<223> OTHER INFORMATION: Synthetic Short sequence in Cterminus of pUL56

<400> SEQUENCE: 1

Trp Met Val Val Lys Tyr Met Gly Phe Phe
1               5                   10


<210> SEQ ID NO 2
<211> LENGTH: 850
<212> TYPE: PRT
<213> ORGANISM: Human cytomegalovirus

<400> SEQUENCE: 2

Met Glu Met Asn Leu Leu Gln Lys Leu Cys Val Val Cys Ser Lys Cys
1               5                   10                  15

Asn Glu Tyr Ala Met Glu Leu Glu Cys Leu Lys Tyr Cys Asp Pro Asn
            20                  25                  30

Val Leu Leu Ala Glu Ser Thr Pro Phe Lys Arg Asn Ala Ala Ala Ile
        35                  40                  45

Val Tyr Leu Tyr Arg Lys Ile Tyr Pro Glu Val Val Ala Gln Asn Arg
    50                  55                  60

Thr Gln Ser Ser Leu Leu Thr Leu Tyr Leu Glu Met Leu Leu Lys Ala
65                  70                  75                  80

Leu His Glu Asp Thr Ala Leu Leu Asp Arg Ala Leu Met Ala Tyr Ser
                85                  90                  95

Arg Gln Pro Asp Arg Ala Ala Phe Tyr Arg Thr Val Leu Arg Leu Asp
            100                 105                 110

Arg Cys Asp Arg His His Thr Val Glu Leu Gln Phe Thr Asp Asn Val
        115                 120                 125
```

-continued

```
Arg Phe Ser Val Ser Leu Ala Thr Leu Asn Asp Ile Glu Arg Phe Leu
    130                 135                 140

Cys Lys Met Asn Tyr Val Tyr Gly Ile Leu Ala Pro Glu Ala Gly Leu
145                 150                 155                 160

Glu Val Cys Ala Gln Leu Leu Glu Leu Leu Arg Arg Leu Cys Gly Ile
                165                 170                 175

Ser Pro Val Ala Arg Gln Glu Val Tyr Val Glu Gly Thr Thr Cys Ala
            180                 185                 190

Gln Cys Tyr Glu Glu Leu Thr Ile Ile Pro Asn Gln Gly Arg Ser Leu
        195                 200                 205

Asn Lys Arg Leu Gln Gly Leu Leu Cys Asn His Ile Ala Val His Arg
    210                 215                 220

Pro Ser Ser Gln Ser Asp Val Asn Ile Gln Thr Val Glu Gln Asp Leu
225                 230                 235                 240

Leu Asp Leu Thr Thr Arg Ile Pro His Leu Ala Gly Val Leu Ser Ala
                245                 250                 255

Leu Lys Ser Leu Phe Ser Ser Ser Ser Ala Tyr His Ser Tyr Ile Gln
            260                 265                 270

Glu Ala Glu Glu Ala Leu Arg Glu Tyr Asn Leu Phe Thr Asp Ile Pro
        275                 280                 285

Glu Arg Ile Tyr Ser Leu Ser Asp Phe Thr Tyr Trp Ser Arg Thr Ser
    290                 295                 300

Glu Val Ile Val Lys Arg Val Gly Ile Thr Ile Gln Gln Leu Asn Val
305                 310                 315                 320

Tyr His Gln Leu Cys Arg Ala Leu Met Asn Gly Ile Ser Arg His Leu
                325                 330                 335

Tyr Gly Glu Asp Val Glu Asp Ile Phe Val Leu Gly Glu Lys Ala Leu
            340                 345                 350

Asp Gly Glu Glu Arg Met Phe Val Gly Ser Val Phe Ala Ala Pro Asn
        355                 360                 365

Arg Ile Ile Asp Leu Ile Thr Ser Leu Ser Ile Gln Ala Phe Glu Asp
    370                 375                 380

Asn Pro Val Phe Asn Lys Leu His Glu Ser Asn Glu Met Tyr Thr Lys
385                 390                 395                 400

Ile Lys His Ile Leu Glu Glu Ile Arg Arg Pro Leu Pro Asp Gly Thr
                405                 410                 415

Gly Gly Asp Gly Pro Glu Gly Glu Ala Ile His Leu Arg Gly Arg Glu
            420                 425                 430

Ala Met Ser Gly Thr Gly Thr Thr Leu Met Thr Ala Ser Asn Ser Ser
        435                 440                 445

Asn Ser Ser Thr His Ser Gln Arg Asn Asn Gly Gly Gly Gly Arg Ala
    450                 455                 460

Arg Gly Gly Gly Lys Lys Ala Val Gly Gly Gly Ala Asn Gly Gln Asp
465                 470                 475                 480

Gly Asp Gly Ser Glu Asn Gly Leu Arg Val Arg Asn Cys Asp Glu His
                485                 490                 495

Glu Ala Leu Asp Leu Val Asp Ala Arg Ser Arg Ile His Asn Val Thr
            500                 505                 510

Arg Glu Val Asn Val Arg Lys Arg Ala Tyr Leu Gln Lys Val Ser Glu
        515                 520                 525

Val Gly Tyr Gly Lys Val Ile Arg Cys Ile Lys Thr Gln Glu Arg Leu
    530                 535                 540

Thr Ser Lys Leu Ile Asp Val Asn Leu Val Gly Pro Leu Cys Leu Asp
```

-continued 545 550 555 560

Phe Ile Ser Lys Leu Met Asn Gly Phe Leu Tyr Arg Ser Gln Tyr His
565 570 575

Gln Asp Gln Asp Val Val Asp Val Gly Asp Gln Phe Thr Tyr Asp Glu
580 585 590

His Leu Tyr Val Val Asn Asn Leu Ile His Lys Ser Leu Pro Val Glu
595 600 605

Ser Leu Pro Leu Leu Gly Gln Gln Ile Tyr Glu Leu Cys Asn Gly Pro
610 615 620

Leu Phe Thr His Cys Thr Asp Arg Tyr Pro Leu Ser His Asn Val Asp
625 630 635 640

Met Ala Tyr Ala Cys Asp Asn Ala Gly Val Leu Pro His Val Lys Asp
645 650 655

Asp Leu Val Lys Cys Ala Glu Gly Thr Val Tyr Pro Ser Glu Trp Met
660 665 670

Val Val Lys Tyr Met Gly Phe Phe Asn Phe Ser Asp Cys Gln Asp Leu
675 680 685

Asn Val Leu Gln Lys Glu Met Trp Met His Val Arg Glu Leu Val Leu
690 695 700

Ser Val Ala Leu Tyr Asn Glu Thr Phe Gly Lys Gln Leu Ser Ile Ala
705 710 715 720

Cys Leu Arg Asp Glu Leu His Pro Asp Arg Asp Val Ile Leu Thr Tyr
725 730 735

Asn Lys Glu Trp Pro Leu Leu Leu Arg His Glu Gly Asn Leu Tyr Lys
740 745 750

Ser Lys Asp Leu Tyr Leu Leu Leu Tyr Arg His Leu Ser Arg Pro Asp
755 760 765

Glu Ser Gly Asp Val Pro Thr Ala Pro Val Ala Lys Pro Ser Thr Leu
770 775 780

Thr Ala Ala Ala Ala Val Ser Gly Ala Phe Arg Glu Pro Asp Arg Pro
785 790 795 800

Trp Leu Pro Ser Pro Tyr Pro Ser Ser Ser Thr Ala Gly Val Ser Arg
805 810 815

Arg Val Arg Ala Thr Arg Lys Arg Pro Arg Arg Ala Ser Ser Leu Leu
820 825 830

Asp Leu Ala Arg Asp Glu His Gly Ile Gln Asp Leu Val Pro Gly Ser
835 840 845

Leu Arg
850

<210> SEQ ID NO 3
<211> LENGTH: 10
<212> TYPE: PRT
<213> ORGANISM: Artificial
<220> FEATURE:
<223> OTHER INFORMATION: Synthetic Variant 1

<400> SEQUENCE: 3

Trp Met Val Val Lys Phe Met Gly Phe Phe
1 5 10

<210> SEQ ID NO 4
<211> LENGTH: 10
<212> TYPE: PRT
<213> ORGANISM: Artificial
<220> FEATURE:
<223> OTHER INFORMATION: Synthetic Variant 2

<400> SEQUENCE: 4

```
Trp Met Val Val Lys Phe Met Gly Phe Tyr
1               5                   10
```

<210> SEQ ID NO 5
<211> LENGTH: 10
<212> TYPE: PRT
<213> ORGANISM: Artificial
<220> FEATURE:
<223> OTHER INFORMATION: Synthetic Variant 3

<400> SEQUENCE: 5

```
Trp Met Val Val Lys Tyr Met Gly Phe Tyr
1               5                   10
```

<210> SEQ ID NO 6
<211> LENGTH: 20
<212> TYPE: PRT
<213> ORGANISM: Artificial
<220> FEATURE:
<223> OTHER INFORMATION: Synthetic HSV_1

<400> SEQUENCE: 6

```
Gly Ser Gly Ala Asp Trp Ala Val Ser Glu Phe Gln Arg Phe Tyr Cys
1               5                   10                  15

Phe Asp Gly Ile
            20
```

<210> SEQ ID NO 7
<211> LENGTH: 20
<212> TYPE: PRT
<213> ORGANISM: Artificial
<220> FEATURE:
<223> OTHER INFORMATION: Synthetic HSV_2

<400> SEQUENCE: 7

```
Gly Ser Gly Ala Asp Trp Ala Val Ser Glu Phe Gln Lys Phe Tyr Cys
1               5                   10                  15

Phe Asp Gly Val
            20
```

<210> SEQ ID NO 8
<211> LENGTH: 19
<212> TYPE: PRT
<213> ORGANISM: Artificial
<220> FEATURE:
<223> OTHER INFORMATION: Synthetic CeHV_1

<400> SEQUENCE: 8

```
Arg Ser Cys Asp Trp Met Thr Ser Glu Phe Arg Arg Phe Tyr Asn Phe
1               5                   10                  15

Ala Gly Ile
```

<210> SEQ ID NO 9
<211> LENGTH: 19
<212> TYPE: PRT
<213> ORGANISM: Artificial
<220> FEATURE:
<223> OTHER INFORMATION: Synthetic CeHV_2

<400> SEQUENCE: 9

```
Asn His Arg Glu Trp Met Val Ser Glu Tyr Lys Glu Phe Tyr Lys Phe
1               5                   10                  15
```

Pro Pro Val

<210> SEQ ID NO 10
<211> LENGTH: 19
<212> TYPE: PRT
<213> ORGANISM: Artificial
<220> FEATURE:
<223> OTHER INFORMATION: Synthetic EHV_1

<400> SEQUENCE: 10

Ala Lys Gly Asp Trp Ser Ile Ser Glu Phe Gln Arg Phe Tyr Cys Phe
1               5                   10                  15

Glu Gly Val

<210> SEQ ID NO 11
<211> LENGTH: 20
<212> TYPE: PRT
<213> ORGANISM: Artificial
<220> FEATURE:
<223> OTHER INFORMATION: Synthetic GaHV_3

<400> SEQUENCE: 11

Cys Ser Ser Ser Asp Trp Ile Val Ser Lys Phe Arg Gly Phe Tyr Asp
1               5                   10                  15

Phe Asp Gly Ile
            20

<210> SEQ ID NO 12
<211> LENGTH: 20
<212> TYPE: PRT
<213> ORGANISM: Artificial
<220> FEATURE:
<223> OTHER INFORMATION: Synthetic MeHV_1

<400> SEQUENCE: 12

Asn Asn Thr Ser Ser Trp Ile Ile Ser Lys Phe Arg Gly Phe Tyr Asp
1               5                   10                  15

Phe Gly Gly Val
            20

<210> SEQ ID NO 13
<211> LENGTH: 19
<212> TYPE: PRT
<213> ORGANISM: Artificial
<220> FEATURE:
<223> OTHER INFORMATION: Synthetic HHV_3

<400> SEQUENCE: 13

Val Gly Ser Asn Trp Leu Leu Ser Pro Phe Arg Gly Phe Tyr Cys Phe
1               5                   10                  15

Ser Gly Val

<210> SEQ ID NO 14
<211> LENGTH: 16
<212> TYPE: PRT
<213> ORGANISM: Artificial
<220> FEATURE:
<223> OTHER INFORMATION: Synthetic SUID

<400> SEQUENCE: 14

Arg Asp Trp Cys Val Ser Glu Phe Arg Gly Phe Tyr Arg Phe Gln Thr
1               5                   10                  15

<210> SEQ ID NO 15

<211> LENGTH: 19
<212> TYPE: PRT
<213> ORGANISM: Artificial
<220> FEATURE:
<223> OTHER INFORMATION: Synthetic GaHV_1

<400> SEQUENCE: 15

Arg Ser Cys Asp Trp Met Thr Ser Glu Phe Arg Arg Phe Tyr Asn Phe
1 5 10 15

Ala Gly Ile

<210> SEQ ID NO 16
<211> LENGTH: 20
<212> TYPE: PRT
<213> ORGANISM: Artificial
<220> FEATURE:
<223> OTHER INFORMATION: Synthetic GaHV_2

<400> SEQUENCE: 16

Ser Arg Lys Thr Asp Trp Thr Val Ser Lys Phe Arg Gly Phe Tyr Asp
1 5 10 15

Phe Ser Thr Ile
20

<210> SEQ ID NO 17
<211> LENGTH: 20
<212> TYPE: PRT
<213> ORGANISM: Artificial
<220> FEATURE:
<223> OTHER INFORMATION: Synthetic AD169

<400> SEQUENCE: 17

Val Tyr Pro Ser Glu Trp Met Val Val Lys Tyr Met Gly Phe Phe Asn
1 5 10 15

Phe Ser Asp Cys
20

<210> SEQ ID NO 18
<211> LENGTH: 20
<212> TYPE: PRT
<213> ORGANISM: Artificial
<220> FEATURE:
<223> OTHER INFORMATION: Synthetic HHV_6_B

<400> SEQUENCE: 18

Ile His Pro Arg Val Trp Met Val Cys Glu Tyr Asn Glu Phe Phe Asn
1 5 10 15

Phe Ser Gly Val
20

<210> SEQ ID NO 19
<211> LENGTH: 20
<212> TYPE: PRT
<213> ORGANISM: Artificial
<220> FEATURE:
<223> OTHER INFORMATION: Synthetic HHB_6_A_GS

<400> SEQUENCE: 19

Ile His Pro Ser Val Trp Met Val Cys Glu Tyr Asn Glu Phe Phe Asn
1 5 10 15

Phe Ser Gly Val
20

<210> SEQ ID NO 20

<211> LENGTH: 20
<212> TYPE: PRT
<213> ORGANISM: Artificial
<220> FEATURE:
<223> OTHER INFORMATION: Synthetic CCMV

<400> SEQUENCE: 20

Val Tyr Pro Ser Glu Trp Met Val Val Lys Tyr Met Ser Phe Phe Asn
1 5 10 15

Phe Ser Glu Cys
20

<210> SEQ ID NO 21
<211> LENGTH: 20
<212> TYPE: PRT
<213> ORGANISM: Artificial
<220> FEATURE:
<223> OTHER INFORMATION: Synthetic RhCMV

<400> SEQUENCE: 21

Val Val Pro Ser Asp Trp Met Thr Val Gly Tyr Met Gly Phe Phe Arg
1 5 10 15

Phe Ala Asp Ile
20

<210> SEQ ID NO 22
<211> LENGTH: 20
<212> TYPE: PRT
<213> ORGANISM: Artificial
<220> FEATURE:
<223> OTHER INFORMATION: Synthetic MCMV

<400> SEQUENCE: 22

Val Val Pro Ser Asp Trp Met Thr Val Gly Tyr Met Gly Phe Phe Arg
1 5 10 15

Phe Ala Asp Ile
20

<210> SEQ ID NO 23
<211> LENGTH: 20
<212> TYPE: PRT
<213> ORGANISM: Artificial
<220> FEATURE:
<223> OTHER INFORMATION: Synthetic RCMV

<400> SEQUENCE: 23

Ala Glu Pro Gly Asp Trp Met Val Ala Gly Tyr Gln Gly Phe Phe Ser
1 5 10 15

Phe Val Asp Val
20

<210> SEQ ID NO 24
<211> LENGTH: 19
<212> TYPE: PRT
<213> ORGANISM: Artificial
<220> FEATURE:
<223> OTHER INFORMATION: Synthetic HHV_8

<400> SEQUENCE: 24

Ile Glu Pro Lys Asp Trp Ile Glu Pro Asn Phe Asn Gln Phe Tyr Ser
1 5 10 15

Phe Glu Asn

<210> SEQ ID NO 25

-continued

```
<211> LENGTH: 19
<212> TYPE: PRT
<213> ORGANISM: Artificial
<220> FEATURE:
<223> OTHER INFORMATION: Synthetic HHV_4_1

<400> SEQUENCE: 25

Ile Glu Pro Ser Asp Trp Ile Glu Thr Ser Phe Asn Ser Phe Tyr Ser
1               5                   10                  15

Val Pro Gly


<210> SEQ ID NO 26
<211> LENGTH: 19
<212> TYPE: PRT
<213> ORGANISM: Artificial
<220> FEATURE:
<223> OTHER INFORMATION: Synthetic HHV_4_2

<400> SEQUENCE: 26

Ile Glu Pro Ser Asp Trp Ile Glu Thr Ser Phe Asn Ser Phe Tyr Ser
1               5                   10                  15

Val Pro Gly
```